United States Patent
Boualleg et al.

(10) Patent No.: US 11,951,456 B2
(45) Date of Patent: *Apr. 9, 2024

(54) PROCESS FOR PREPARING A CATALYST FOR THE HYDROGENATION OF AROMATICS, COMPRISING A STEP OF FORMING A NI—CU ALLOY IN PRE-IMPREGNATION

(71) Applicant: IFP Energies Nouvelles, Rueil-Malmaison (FR)

(72) Inventors: Malika Boualleg, Rueil-Malmaison (FR); Anne-Agathe Quoineaud, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 362 days.

This patent is subject to a terminal disclaimer.

(21) Appl. No.: 17/422,773

(22) PCT Filed: Jan. 8, 2020

(86) PCT No.: PCT/EP2020/050331
§ 371 (c)(1),
(2) Date: Jul. 14, 2021

(87) PCT Pub. No.: WO2020/148133
PCT Pub. Date: Jul. 23, 2020

(65) Prior Publication Data
US 2022/0072516 A1    Mar. 10, 2022

(30) Foreign Application Priority Data
Jan. 15, 2019   (FR) ...................................... 1900333

(51) Int. Cl.
| | |
|---|---|
| *B01J 23/755* | (2006.01) |
| *B01J 21/04* | (2006.01) |
| *B01J 37/02* | (2006.01) |
| *B01J 37/04* | (2006.01) |
| *B01J 37/08* | (2006.01) |
| *B01J 37/18* | (2006.01) |
| *B01J 37/20* | (2006.01) |
| *C07C 5/10* | (2006.01) |

(52) U.S. Cl.
CPC ............ *B01J 23/755* (2013.01); *B01J 21/04* (2013.01); *B01J 37/0205* (2013.01); *B01J 37/024* (2013.01); *B01J 37/04* (2013.01); *B01J 37/082* (2013.01); *B01J 37/18* (2013.01); *B01J 37/20* (2013.01); *C07C 5/10* (2013.01); *C07C 2521/04* (2013.01); *C07C 2523/755* (2013.01)

(58) Field of Classification Search
None
See application file for complete search history.

(56) References Cited

U.S. PATENT DOCUMENTS

| | | |
|---|---|---|
| 5,948,942 A | 9/1999 | Ramirez De Agudelo et al. |
| 10,307,738 B2 | 6/2019 | Boualleg et al. |
| 2005/0209491 A1 | 9/2005 | Ryu |
| 2006/0084830 A1 | 4/2006 | Ryu |
| 2017/0259249 A1 | 9/2017 | Boualleg et al. |

FOREIGN PATENT DOCUMENTS

| | | |
|---|---|---|
| EP | 1114013 B1 | 11/2002 |
| WO | 2016/037830 A1 | 3/2016 |

OTHER PUBLICATIONS

International Search Report dated Mar. 10, 2020 issued in corresponding PCT/EP2020/050331 application (4 pages).
S. Molood Masoom Nataj et al., "Modeling and Optimization of Methane Dry Reforming Over Ni—Cu/Al2O3 Catalyst Using Box-Behnken Design", Journal of Energy Chemistry, vol. 27, No. 5 (2018) pp. 1475-1488.
Obregon et al., "Structure-Activity Relationships of Ni—Cu/Al2O3 Catalysts For y-Valerolactone Conversion to 2-Methyltetrahydrofuran", Applied Catalysis B: Environmental, vol. 210 (2017) pp. 328-341.

*Primary Examiner* — In Suk C Bullock
*Assistant Examiner* — Alyssa L Cepluch
(74) *Attorney, Agent, or Firm* — MILLEN, WHITE, ZELANO & BRANIGAN, P.C.; Csaba Henter

(57) ABSTRACT

A process for preparing a catalyst for the hydrogenation of aromatic or polyaromatic compounds comprising nickel, copper and a support comprising at least one refractory oxide, comprising the following steps:
- bringing the support into contact with a solution containing at least one copper precursor and one nickel precursor;
- drying the catalyst precursor at a temperature of less than 250° C.;
- reducing the catalyst precursor by bringing said precursor into contact with a reducing gas at a temperature of between 150° C. and 250° C.;
- bringing the catalyst precursor into contact with a solution comprising a nickel precursor;
- a step of drying the catalyst precursor at a temperature of less than 250° C.;
- reducing the catalyst precursor by bringing said precursor into contact with a reducing gas at a temperature of between 150° C. and 250° C.

17 Claims, No Drawings

PROCESS FOR PREPARING A CATALYST FOR THE HYDROGENATION OF AROMATICS, COMPRISING A STEP OF FORMING A NI—CU ALLOY IN PRE-IMPREGNATION

TECHNICAL FIELD

The present invention relates to a process for preparing a supported metallic catalyst, comprising nickel and copper, intended particularly for the hydrogenation of at least one aromatic or polyaromatic compound present in a hydrocarbon feedstock.

STATE OF THE ART

Catalysts for the hydrogenation of aromatic compounds are generally based on metals from Group VIII of the Periodic Table of the Elements, such as nickel. The metal is in the form of nanometric metal particles deposited on a support which may be a refractory oxide. The content of group VIII metal, the optional presence of a second metal element, the size of the metal particles and the distribution of the active phase in the support and also the nature and the pore distribution of the support are parameters which may have an influence on the performance of the catalysts.

The rate of the hydrogenation reaction is governed by several criteria, such as the diffusion of the reactants toward the surface of the catalyst (external diffusional limitations), the diffusion of the reactants in the porosity of the support toward the active sites (internal diffusional limitations) and the intrinsic properties of the active phase, such as the size of the metallic particles and the distribution of the active phase within the support.

The promotion of a nickel-based catalyst has frequently been proposed in order to improve performance levels in hydrogenation of unsaturated hydrocarbons. For example, the promotion of a nickel-based catalyst has frequently been proposed in order to improve performance levels in selective hydrogenation. By way of illustration, U.S. Pat. No. 5,208,405 discloses a catalyst based on nickel and silver for the selective hydrogenation of $C_4$-$C_{10}$ diolefins. Furthermore, it is known to promote nickel, predominantly present, with metals of group IB, in particular gold (FR 2 949 077) or tin (FR 2 949 078). Document FR 3 011 844 discloses a catalyst for the implementation of a selective hydrogenation process comprising a support and an active metallic phase deposited on the support, the active metallic phase comprising copper and at least one nickel or cobalt metal in a Cu:(Ni and/or Co) mole ratio greater than 1.

Moreover, prior to the employment of such catalysts and the use thereof in a hydrogenation process, a step of reducing treatment in the presence of a reducing gas is carried out so as to obtain a catalyst comprising an active phase at least partially in metallic form. This treatment makes it possible to activate the catalyst and to form metallic particles. This treatment may be carried out in situ or ex situ, that is to say after or before the catalyst is charged to the hydrogenation reactor.

SUBJECTS OF THE INVENTION

Continuing its research in the field of hydrogenating catalysts, the applicant has now surprisingly discovered that it is possible to prepare catalysts which are particularly active in the hydrogenation of aromatic compounds after reduction at low temperature, by carrying out a specific preparation process wherein an alloy based on nickel and copper is formed on the support before depositing on the support the precursor of the active phase (based on nickel) of the catalyst.

Without wishing to be bound by any theory, it has been observed by the applicant that, during the preparation of the catalyst, carrying out a step of bringing the support into contact with a solution simultaneously containing a copper-based metal precursor and a nickel-based metal precursor, followed by a step of drying and reducing in the presence of a reducing gas at low temperature (between 150° C. and 250° C.) makes it possible to obtain a nickel-copper alloy (in reduced form) which unexpectedly makes it possible to greatly improve the reducibility of the nickel active phase on the support, said nickel active phase being supplied in a step subsequent to the formation of the nickel-copper alloy (in reduced form). The preparation process according to the invention thus makes it possible to carry out a step of reducing the metal elements in the presence of a reducing gas at lower temperatures and shorter reaction times than those commonly used in the prior art. Advantageously, the use of less severe operating conditions than in the prior art makes it possible to directly carry out the reduction step within the reactor in which it is desired to carry out the hydrogenation of aromatic compounds. Furthermore, the presence of copper in the catalyst makes it possible to maintain good activity and a longer service life of the catalyst when the latter is placed in contact with a hydrocarbon feedstock comprising sulfur, notably in aromatic hydrocarbon fractions. Indeed, compared to nickel, the copper present in the catalyst more easily captures the sulfur-containing compounds included in the feedstock, thereby strongly limiting the irreversible poisoning of the most virulent active sites of the nickel which exist on the new catalyst.

A subject of the present invention is a process for preparing a catalyst for the hydrogenation of aromatic or polyaromatic compounds comprising a metallic active phase based on nickel, in a proportion of 10% and 65% by weight of nickel element relative to the total weight of the catalyst, and based on copper, in a proportion of 0.5% to 15% by weight of copper element relative to the total weight of the catalyst, and a support comprising at least one refractory oxide chosen from silica, alumina and silica-alumina, said process comprising the following steps:

a) a step of bringing the support into contact with at least one solution containing at least one copper precursor and one nickel precursor at a desired nickel concentration is carried out in order to obtain, on the final catalyst, a content of between 0.5% and 15% by weight of nickel element relative to the total weight of the final catalyst;

b) at least one step of drying the catalyst precursor resulting from step a) is carried out at a temperature of less than 250° C.;

c) optionally, a heat treatment of the catalyst precursor obtained at the end of step b) is carried out at a temperature of between 250 and 1000° C., in the presence or absence of water;

d) the catalyst precursor resulting from step b), optionally step c), is reduced by bringing said catalyst precursor into contact with a reducing gas at a temperature of between 150 and 250° C.;

e) a step of bringing the catalyst precursor obtained at the end of step d) into contact with a solution comprising at least one nickel precursor is carried out;

f) at least one step of drying the catalyst precursor resulting from step e) is carried out at a temperature of less than 250° C.;

g) optionally, a heat treatment of the catalyst precursor obtained at the end of step f) is carried out at a temperature of between 250 and 1000° C., in the presence or absence of water;

h) the catalyst precursor resulting from step f), optionally step g), is reduced by bringing said catalyst precursor into contact with a reducing gas at a temperature of between 150 and 250° C.

Advantageously, in step a) the mole ratio between nickel and copper is between 0.5 and 5, preferably between 0.7 and 4.5, more preferably between 0.9 and 4.

Preferably, step d) and/or h) is (are) carried out at a temperature of between 160 and 230° C.

More preferentially, step d) and/or h) is (are) carried out at a temperature of between 170 and 220° C.

Advantageously, steps d) and/or h) is (are) carried out for between 10 minutes and 110 minutes.

In one embodiment, the preparation process also comprises a step of passivation of the catalyst precursor with a sulfur-containing compound after the reduction step d) but before step e), and/or after the reduction step h).

Advantageously, the passivation step(s) is (are) carried out at a temperature of between 20 and 350° C. for 10 to 240 minutes.

Advantageously, said sulfur-containing compound is chosen from thiophene, thiophane, dimethyl sulfide, diethyl sulfide, dipropyl sulfide, propylmethyl sulfide, dithiodiethanol.

Preferably, the copper precursor is chosen from copper acetate, copper acetylacetonate, copper nitrate, copper sulfate, copper chloride, copper bromide, copper iodide or copper fluoride.

More preferably, the copper precursor is copper nitrate.

Advantageously, the reducing gas of step d) and/or h) is dihydrogen.

Advantageously, the hydrogen flow rate, expressed in l/hour/gram of catalyst precursor, is between 0.01 and 100 l/hour/gram of catalyst precursor.

Advantageously, the nickel precursor supplied during step a) and/or e) is chosen from nickel nitrate, nickel carbonate or nickel hydroxide.

Another subject according to the invention relates to a process for the hydrogenation of at least one aromatic or polyaromatic compound present in a hydrocarbon feedstock having a final boiling point of less than or equal to 650° C., said process being carried out in the gas phase or in the liquid phase, at a temperature of between 30 and 350° C., at a pressure of between 0.1 and 20 MPa, at a hydrogen/(aromatic compounds to be hydrogenated) mole ratio between 0.1 and 10 and at an hourly space velocity HSV of between 0.05 and 50 $h^{-1}$, in the presence of a catalyst obtained according to the preparation process according to the invention.

DETAILED DESCRIPTION OF THE INVENTION

1. Definitions

Subsequently, the groups of chemical elements are given according to the CAS classification (CRC Handbook of Chemistry and Physics, published by CRC Press, editor-in-chief D. R. Lide, 81st edition, 2000-2001). For example, group VIII according to the CAS classification corresponds to the metals of columns 8, 9 and 10 according to the new IUPAC classification.

The degree of reduction (DR) of a metal M contained in the catalyst is defined as being the percentage of said metal M reduced after the step of reducing said catalyst. The degree of reduction (DR) corresponds to the ratio between the amount of metal reduced (M1) and the amount of theoretically reducible metal present on the catalyst, measured by X-ray fluorescence (M2), i.e. DR (%)=(M1/M2)×100. In the context of the present invention, the degree of reduction of the nickel (Ni) was measured by X-ray diffraction (XRD) analysis. The description of the method for measuring the amount of reducible metal on oxide catalysts is explained later in the description (cf. examples section).

The expression "the specific surface of the catalyst or of the support used for the preparation of the catalyst according to the invention" is intended to mean the BET specific surface determined by nitrogen adsorption in accordance with standard ASTM D 3663-78 drawn up from the Brunauer-Emmett-Teller method described in the journal "The Journal of the American Chemical Society", 60, 309 (1938).

In the present application, the term "to comprise" is synonymous with (means the same thing as) "to include" and "to contain", and is inclusive or open and does not exclude other elements not stated. It is understood that the term "to comprise" includes the exclusive and closed term "to consist of".

The term "macropores" is intended to mean pores, the opening of which is greater than 50 nm.

The term "mesopores" is intended to mean pores, the opening of which is between 2 nm and 50 nm, limits included.

The term "micropores" is intended to mean pores, the opening of which is less than 2 nm.

The term "total pore volume" of the catalyst or of the support used for the preparation of the catalyst according to the invention is intended to mean the volume measured by intrusion with a mercury porosimeter according to standard ASTM D4284-83 at a maximum pressure of 4000 bar (400 MPa), using a surface tension of 484 dyne/cm and a contact angle of 140°. The wetting angle was taken equal to 140° following the recommendations of the work "Techniques de l'ingénieur, traité analyse et caractérisation" [Techniques of the Engineer, Analysis and Characterization Treatise], pages 1050-1055, written by Jean Charpin and Bernard Rasneur.

In order to obtain better accuracy, the value of the total pore volume corresponds to the value of the total pore volume measured by intrusion with a mercury porosimeter measured on the sample minus the value of the total pore volume measured by intrusion with a mercury porosimeter measured on the same sample for a pressure corresponding to 30 psi (approximately 0.2 MPa).

The volume of the macropores and of the mesopores is measured by porosimetry by intrusion of mercury according to standard ASTM D4284-83 at a maximum pressure of 4000 bar (400 MPa), using a surface tension of 484 dyne/cm and a contact angle of 140°. The value from which the mercury fills all the intergranular voids is set at 0.2 MPa and it is considered that, above this, the mercury penetrates into the pores of the sample.

The macropore volume of the catalyst or of the support used for the preparation of the catalyst according to the invention is defined as being the cumulative volume of mercury introduced at a pressure of between 0.2 MPa and 30

MPa, corresponding to the volume present in the pores with an apparent diameter of greater than 50 nm.

The mesopore volume of the catalyst or of the support used for the preparation of the catalyst according to the invention is defined as being the cumulative volume of mercury introduced at a pressure of between 30 MPa and 400 MPa, corresponding to the volume present in the pores with an apparent diameter of between 2 and 50 nm.

The micropore volume is measured by nitrogen porosimetry. The quantitative analysis of the microporosity is performed using the "t" method (method of Lippens-De Boer, 1965), which corresponds to a transform of the starting adsorption isotherm, as described in the work "Adsorption by powders and porous solids. Principles, methodology and applications", written by F. Rouquérol, J. Rouquérol and K. Sing, Academic Press, 1999.

The median mesopore diameter is also defined as being the diameter such that, out of the combined pores constituting the mesopore volume, all the pores with a size of less than this diameter constitute 50% of the total mesopore volume determined by intrusion with a mercury porosimeter.

The median macropore diameter is also defined as being the diameter such that, out of the combined pores constituting the macropore volume, all the pores with a size of less than this diameter constitute 50% of the total macropore volume determined by intrusion with a mercury porosimeter.

2. Detailed Description

Process for Preparing the Catalyst

According to the invention, the process for preparing a catalyst for the hydrogenation of aromatic or polyaromatic compounds comprising, preferably consisting of, a metallic active phase based on nickel, in a proportion of 10% and 65% by weight of nickel element relative to the total weight of the catalyst, and based on copper, in a proportion of 0.5% to 15% by weight of copper element relative to the total weight of the catalyst, and a support comprising at least one refractory oxide chosen from silica, alumina and silica-alumina, comprises, preferably consists of, the following steps:

a) a step of bringing the support into contact with at least one solution containing at least, preferably consisting of, one copper precursor and one nickel precursor at a desired nickel concentration is carried out in order to obtain, on the final catalyst, a content of between 0.5% and 15% by weight of nickel element relative to the total weight of the final catalyst;

b) at least one step of drying the catalyst precursor resulting from step a) is carried out at a temperature of less than 250° C.;

c) optionally, a heat treatment of the catalyst precursor obtained at the end of step b) is carried out at a temperature of between 250 and 1000° C., in the presence or absence of water;

d) the catalyst precursor resulting from step b), optionally step c), is reduced by bringing said catalyst precursor into contact with a reducing gas at a temperature of between 150 and 250° C.;

e) a step of bringing the catalyst precursor obtained at the end of step d) into contact with a solution comprising at least one nickel precursor, preferably a solution consisting of one nickel precursor, is carried out;

f) at least one step of drying the catalyst precursor resulting from step e) is carried out at a temperature of less than 250° C.;

g) optionally, a heat treatment of the catalyst precursor obtained at the end of step f) is carried out at a temperature of between 250 and 1000° C., in the presence or absence of water;

h) the catalyst precursor resulting from step f), optionally step g), is reduced by bringing said catalyst precursor into contact with a reducing gas at a temperature of between 150 and 250° C.;

i) optionally, a step i) of passivation with a sulfur-containing compound is carried out after the reducing treatment step h).

Steps a) to i) of said preparation process are described in detail below.

Step a) Bringing a Nickel Precursor and a Copper Precursor into Contact with the Support The deposition of nickel and copper on said support, in accordance with the implementation of step a), can be carried out by dry impregnation or excess impregnation, or also by deposition-precipitation, according to methods well known to those skilled in the art.

Said step a) is preferentially carried out by impregnation of the support consisting for example in bringing said support into contact with at least one solution, aqueous or organic (for example methanol or ethanol or phenol or acetone or toluene or dimethyl sulfoxide (DMSO)) or else consisting of a mixture of water and at least one organic solvent, comprising, preferably consisting of, at least one nickel precursor and at least one copper precursor at least partially in the dissolved state, or else in bringing said support into contact with at least one colloidal solution comprising, preferably consisting of, at least one nickel precursor and one copper precursor in oxidized form (nanoparticles of oxide, of oxy(hydroxide) or of hydroxide of nickel and copper) or in reduced form (metallic nanoparticles of nickel and copper in the reduced state). Preferably, the solution is aqueous. The pH of this solution may be modified by the optional addition of an acid or of a base.

Preferably, said step a) is carried out by dry impregnation, which consists in bringing the catalyst support into contact with a solution comprising, preferably consisting of, at least one nickel precursor and at least one copper precursor, the volume of the solution of which is between 0.25 and 1.5 times the pore volume of the support to be impregnated.

When the nickel precursor is introduced in aqueous solution, a nickel precursor is advantageously used in the form of nitrate, carbonate, acetate, chloride, hydroxide, hydroxycarbonate, oxalate, sulfate or formate, of complexes formed by a polyacid or an acid-alcohol and its salts, of complexes formed with acetylacetonates, of tetramine or hexamine complexes, or else of any other inorganic derivative soluble in aqueous solution, which is placed in contact with said support. Preferably, nickel nitrate, nickel hydroxide, nickel carbonate, nickel chloride or nickel hydroxycarbonate is advantageously used as nickel precursor. Very preferably, the nickel precursor is nickel nitrate, nickel carbonate or nickel hydroxide.

When the copper precursor is introduced in aqueous solution, a copper precursor in mineral or organic form is advantageously used. In mineral form, the copper precursor can be chosen from copper acetate, copper acetylacetonate, copper nitrate, copper sulfate, copper chloride, copper bromide, copper iodide or copper fluoride. Very preferably, the copper precursor salt is copper nitrate.

According to the invention, the nickel precursor is supplied in step a) at a desired concentration in order to obtain on the final catalyst (i.e. obtained at the end of the reduction step h) or the passivation step i) if the latter is carried out)

a content of between 0.5% and 15% by weight of nickel element relative to the total weight of the final catalyst, preferably between 0.5% and 10% by weight, more preferentially between 1% and 8% by weight, even more preferentially between 1% and 7% by weight.

The amounts of the copper precursor(s) introduced into the solution according to step a) are chosen such that the total copper content is between 0.5% and 15% by weight of copper element relative to the total weight of the final catalyst (i.e. obtained at the end of the reduction step h) or the passivation step i) if the latter is carried out), preferably between 0.5% and 12% by weight, preferably between 0.75% and 10% by weight, and even more preferentially between 1% and 9% by weight.

Step b) Drying the Impregnated Support

Step b) of drying the impregnated support is carried out at a temperature of less than 250° C., preferably of between 15 and 180° C., more preferentially between 30 and 160° C., even more preferentially between 50 and 150° C., and even more preferentially between 70 and 140° C., for a period typically of between 10 minutes and 24 hours. Longer periods of time are not ruled out, but do not necessarily afford any improvement.

The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or of nitrogen.

Step c) Heat Treatment of the Dried Catalyst (Optional Step)

The catalyst precursor obtained at the end of step b) can undergo an additional heat treatment step, before the reduction step d), at a temperature of between 250 and 1000° C. and preferably between 250 and 750° C., for a period typically between 15 minutes and 10 hours, under an inert atmosphere or under an oxygen-containing atmosphere, optionally in the presence of water. Longer treatment times are not ruled out, but do not necessarily afford an improvement.

The term "heat treatment" is intended to mean temperature treatment respectively without the presence or in the presence of water. In the latter case, contact with the steam can take place at atmospheric pressure or under autogenous pressure. Several combined cycles without the presence or with the presence of water can be performed.

In the event of water being present, the water content is preferably between 150 and 900 grams per kilogram of dry air and even more preferably between 250 and 650 grams per kilogram of dry air.

Thus, after the drying step b), or after the optional heat treatment step c), the catalyst precursor comprises nickel in oxide form, that is to say in NiO form, and copper in oxide form, that is to say in CuO form.

Step d) Reduction with a Reducing Gas

According to the invention, a step of reducing treatment d) of the dried catalyst obtained at the end of step b) or of the catalyst obtained at the end of step c) is carried out in the presence of a reducing gas so as to form on the catalyst support a nickel-copper alloy at least partially in metallic form. The reducing gas is preferably hydrogen. The hydrogen can be used pure or as a mixture (for example a hydrogen/nitrogen, hydrogen/argon or hydrogen/methane mixture). In the case where the hydrogen is used as a mixture, all proportions can be envisaged.

According to one essential aspect of the preparation process according to the invention, said reducing treatment is carried out at a temperature of between 150° C. and 250° C., preferably of between 160 and 230° C., and more preferentially between 170 and 220° C. The duration of the reducing treatment is between 5 minutes and less than 5 hours, preferably between 10 minutes and 4 hours, and even more preferentially between 10 minutes and 110 minutes.

It has been observed by the applicant that step d) of reduction with a reducing gas makes it possible to form a nickel-copper alloy at least partially in metallic form. The nickel-copper alloy satisfies the formula $Ni_xCu_y$, with x between 0.1 and 0.9 and y between 0.1 and 0.9.

The rise in temperature up to the desired reduction temperature is generally slow, for example set between 0.1 and 10° C./min, preferably between 0.3 and 7° C./min.

The hydrogen flow rate, expressed in l/hour/gram of catalyst precursor, is between 0.01 and 100 l/hour/gram of catalyst, preferably between 0.05 and 10 l/hour/gram of catalyst precursor and more preferably still between 0.1 and 5 l/hour/gram of catalyst precursor.

Passivation (Optional Step)

The catalyst precursor obtained at the end of the reduction step d) can advantageously be passivated before carrying out the step of bringing said catalyst precursor into contact with a solution comprising, preferably consisting of, at least one nickel precursor (step e).

When carried out, the step of passivation of the catalyst precursor obtained at the end of step d) is carried out with a sulfur-containing compound which makes it possible to improve the selectivity of the catalysts and to avoid thermal runaway during the start-up of new catalysts. The passivation generally consists in irreversibly poisoning, by the sulfur-containing compound, the most virulent active sites of the nickel which exist on the new catalyst and thus in weakening the activity of the catalyst in favor of its selectivity. The passivation step is carried out by the use of methods known to those skilled in the art.

The passivation step with a sulfur-containing compound is generally carried out at a temperature of between 20 and 350° C., preferably between 40 and 200° C., for 10 to 240 minutes. The sulfur-containing compound is, for example, chosen from the following compounds: thiophene, thiophane, alkyl monosulfides, such as dimethyl sulfide, diethyl sulfide, dipropyl sulfide and propyl methyl sulfide, or also an organic disulfide of formula HO—$R_1$—S—S—$R_2$—OH, such as dithiodiethanol of formula HO—$C_2H_4$—S—S—$C_2H_4$—OH (often referred to as DEODS). The sulfur content is generally between 0.1% and 2% by weight of said element relative to the total weight of the catalyst.

Step e) Bringing the Catalyst Precursor into Contact with a Solution Comprising a Nickel Precursor The deposition of nickel, in accordance with the implementation of step e), can be carried out by dry impregnation or excess impregnation, or else by deposition-precipitation, according to methods well known to those skilled in the art.

Said step e) is preferentially carried out by impregnating the catalyst precursor obtained at the end of step d) (or after the optional passivation step) consisting for example in bringing the catalyst precursor into contact with at least one solution, aqueous or organic (for example methanol or ethanol or phenol or acetone or toluene or dimethyl sulfoxide (DMSO)), or else consisting of a mixture of water and at least one organic solvent, comprising, preferably consisting of, at least one nickel precursor at least partially in the dissolved state, or else in bringing the catalyst precursor into contact with at least one colloidal solution comprising, preferably consisting of, at least one nickel precursor, in oxidized form (nanoparticles of oxides, oxy(hydroxide) or hydroxide of nickel) or in reduced form (metallic nanoparticles of nickel in the reduced state). Preferably, the solution is aqueous. The pH of this solution will be able to be modified by the optional addition of an acid or of a base.

Preferably, said step e) is carried out by dry impregnation, which consists in bringing the catalyst precursor into contact with at least one solution containing, preferably consisting of, at least one nickel precursor, the volume of the solution of which is between 0.25 and 1.5 times the pore volume of the support of the catalyst precursor to be impregnated.

When the nickel precursor is introduced in aqueous solution, use is advantageously made of a nickel precursor in the nitrate, carbonate, chloride, sulfate, hydroxide, hydroxycarbonate, formate, acetate or oxalate form, in the form of complexes formed with acetylacetonates, or also in the form of tetramine or hexamine complexes, or in the form of any other inorganic derivative which is soluble in aqueous solution, which is brought into contact with said catalyst precursor. Use is advantageously made, as nickel precursor, of nickel nitrate, nickel carbonate, nickel chloride, nickel hydroxide or nickel hydroxycarbonate. Very preferably, the nickel precursor is nickel nitrate, nickel carbonate or nickel hydroxide.

The nickel precursor is supplied in step e) at a desired concentration in order to obtain on the final catalyst (i.e. obtained at the end of the reduction step h) or the passivation step i) if the latter is carried out) a content of between 9% and 60% by weight of nickel element relative to the total weight of the catalyst, preferably between 9% and 57% by weight, more preferably between 9.5% and 55% by weight, and more preferably still between 9.5% and 50% by weight.

Step f) Drying the Impregnated Support

Step f) of drying the impregnated support is carried out at a temperature of less than 250° C., preferably of between 15 and 180° C., more preferentially between 30 and 160° C., even more preferentially between 50 and 150° C., and even more preferentially between 70 and 140° C., for a period typically between 10 minutes and 24 hours. Longer periods of time are not ruled out, but do not necessarily afford any improvement.

The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or of nitrogen.

g) Heat Treatment of the Dried Catalyst (Optional Step)

The dried catalyst precursor can undergo an additional heat treatment step, before the reduction step h), at a temperature of between 250 and 1000° C. and preferably between 250 and 750° C., for a period typically between 15 minutes and 10 hours, under an inert atmosphere or under an oxygen-containing atmosphere, optionally in the presence of water. Longer treatment times are not ruled out, but do not necessarily afford an improvement.

The term "heat treatment" is intended to mean temperature treatment respectively without the presence or in the presence of water. In the latter case, contact with the steam can take place at atmospheric pressure or under autogenous pressure. Several combined cycles without the presence or with the presence of water can be performed. After this or these treatment(s), the catalyst precursor comprises nickel in the oxide form, that is to say in the NiO form.

In the event of water being present, the water content is preferably between 150 and 900 grams per kilogram of dry air and even more preferably between 250 and 650 grams per kilogram of dry air.

Step h) Reduction with a Reducing Gas

Prior to the use of the catalyst in the catalytic reactor and the implementation of a hydrogenation process, a reducing treatment step h) is carried out in the presence of a reducing gas so as to obtain a catalyst comprising nickel at least partially in the metallic form. This step is advantageously carried out in situ, that is to say after charging of the catalyst to a reactor for hydrogenation of aromatic or polyaromatic compounds. This treatment makes it possible to activate said catalyst and to form metal particles, in particular of nickel in the zero-valent state. The in-situ implementation of the catalyst reducing treatment makes it possible to dispense with an additional step of passivation of the catalyst with an oxygen-bearing compound or $CO_2$, which is necessarily the case when the catalyst is prepared by carrying out a reducing treatment ex situ, that is to say outside the reactor used for hydrogenation of aromatic or polyaromatic compounds. In fact, when the reducing treatment is carried out ex-situ, it is necessary to carry out a passivation step in order to preserve the metallic phase of the catalyst in the presence of air (during operations of transport and charging of the catalyst to the hydrogenation reactor), then to carry out a new step of reducing the catalyst.

The reducing gas is preferably hydrogen. The hydrogen can be used pure or as a mixture (for example a hydrogen/nitrogen, hydrogen/argon or hydrogen/methane mixture). In the case where the hydrogen is used as a mixture, all proportions can be envisaged.

According to one essential aspect of the preparation process according to the invention, said reducing treatment is carried out at a temperature of between 150° C. and 250° C., preferably of between 160 and 230° C., and more preferentially between 170 and 220° C. The duration of the reducing treatment is between 5 minutes and less than 5 hours, preferably between 10 minutes and 4 hours, and even more preferentially between 10 minutes and 110 minutes.

The presence of the nickel-copper alloy at least partially in reduced form makes it possible to use operating conditions for reducing the nickel active phase which are less severe than in the prior art and thus makes it possible to carry out the reduction step directly within the reactor in which it is desired to carry out the hydrogenation of aromatic or polyaromatic compounds.

Furthermore, the presence of copper in the catalyst makes it possible to preserve good activity of the catalyst and a good service life of the catalyst when the latter is placed in contact with a hydrocarbon feedstock comprising sulfur, notably steam cracking and/or catalytic cracking C3 hydrocarbon fractions. Indeed, compared to nickel, the copper present in the catalyst more easily captures the sulfur-containing compounds included in the feedstock, thereby avoiding irreversibly poisoning the most virulent active sites of the nickel which exist on the new catalyst.

The rise in temperature up to the desired reduction temperature is generally slow, for example set between 0.1 and 10° C./min, preferably between 0.3 and 7° C./min.

The hydrogen flow rate, expressed in l/hour/gram of catalyst precursor, is between 0.01 and 100 l/hour/gram of catalyst, preferably between 0.05 and 10 l/hour/gram of catalyst precursor and more preferably still between 0.1 and 5 l/hour/gram of catalyst precursor.

Step i) Passivation (Optional)

The catalyst prepared according to the process according to the invention can advantageously undergo a passivation step with a sulfur-containing compound which makes it possible to improve the selectivity of the catalysts and to avoid thermal runaway during the start-up of new catalysts. The passivation generally consists in irreversibly poisoning, by the sulfur-containing compound, the most virulent active sites of the nickel which exist on the new catalyst and thus in weakening the activity of the catalyst in favor of its selectivity. The passivation step is carried out using methods known to those skilled in the art.

The passivation step with a sulfur-containing compound is generally carried out at a temperature of between 20 and 350° C., preferably between 40 and 200° C., for 10 to 240 minutes. The sulfur-containing compound is, for example, chosen from the following compounds: thiophene, thiophane, alkyl monosulfides, such as dimethyl sulfide, diethyl sulfide, dipropyl sulfide and propyl methyl sulfide, or also an organic disulfide of formula HO—$R_1$—S—S—$R_2$—OH, such as dithiodiethanol of formula HO—$C_2H_4$—S—S—$C_2H_4$—OH (often referred to as DEODS). The sulfur content is generally between 0.1% and 2% by weight of said element relative to the total weight of the catalyst.

Catalyst

The catalyst that can be obtained by means of the preparation process according to the invention comprises an active phase comprising nickel and copper, part of the nickel and copper of which is in the form of a nickel-copper alloy, advantageously corresponding to the formula $Ni_xCu_y$, with x between 0.1 and 0.9 and y between 0.1 and 0.9, and a support in the form of a refractory oxide chosen from silica, alumina and silica-alumina.

The copper content is between 0.5 and 15% by weight of copper element relative to the total weight of the catalyst, preferably between 0.5 and 12% by weight, preferably between 0.75 and 10% by weight, and even more preferentially between 1 and 9% by weight.

The total nickel content is between 10% and 65% by weight, preferably between 14% and 50% by weight, preferably between 20% and 45% by weight, of said element relative to the total weight of the catalyst.

The nickel content included in the copper-nickel alloy formed by the preparation process according to the invention is between 0.5% and 15% by weight of nickel element relative to the total weight of the catalyst, preferably between 1% and 12% by weight, and more preferentially between 1% and 10% by weight.

The porous support is chosen from the group consisting of silica, alumina and silica-alumina. Even more preferably, the support is alumina. The alumina may be present in all possible crystallographic forms: alpha, delta, theta, chi, rho, eta, kappa, gamma, etc., taken alone or as a mixture. Preferably, the support is chosen from alpha, delta, theta and gamma alumina.

The specific surface area of the support is generally greater than or equal to 30 $m^2/g$, preferably greater than or equal to 50 $m^2/g$, more preferably between 60 $m^2/g$ and 500 $m^2/g$, and more preferably still between 70 $m^2/g$ and 400 $m^2/g$. The specific surface area BET is measured by nitrogen physisorption.

The total pore volume of the support is generally between 0.1 and 1.5 $cm^3/g$, preferably between 0.35 and 1.2 $cm^3/g$, and even more preferably between 0.4 and 1.0 $cm^3/g$, and even more preferably between 0.45 and 0.9 $cm^3/g$.

Said catalyst is generally presented in all the forms known to those skilled in the art, for example in the form of beads (generally having a diameter of between 1 and 8 mm), of extrudates, of blocks or of hollow cylinders. Preferably, it consists of extrudates with a diameter generally of between 0.5 and 10 mm, preferably between 0.8 and 3.2 mm and very preferably between 1.0 and 2.5 mm and with a mean length of between 0.5 and 20 mm. The term "mean diameter" of the extrudates is intended to mean the mean diameter of the circle circumscribed in the cross section of these extrudates. The catalyst can advantageously be presented in the form of cylindrical, multilobal, trilobal or quadrilobal extrudates. Preferably, its shape will be trilobal or quadrilobal. The shape of the lobes could be adjusted according to all the methods known from the prior art.

The specific surface area of the support is generally greater than or equal to 30 $m^2/g$, preferably greater than or equal to 50 $m^2/g$, more preferably between 60 $m^2/g$ and 500 $m^2/g$, and more preferably still between 70 $m^2/g$ and 400 $m^2/g$.

The total pore volume of the catalyst is generally between 0.1 and 1.5 $cm^3/g$, preferably between 0.35 and 1.2 $cm^3/g$, and even more preferably between 0.4 and 1.0 $cm^3/g$, and even more preferably between 0.45 and 0.9 $cm^3/g$.

The catalyst advantageously has a macroporous volume less than or equal to 0.6 ml/g, preferably less than or equal to 0.5 ml/g, more preferably less than or equal to 0.4 ml/g, and even more preferably less than or equal to 0.3 ml/g.

The mesoporous volume of the catalyst is generally at least 0.10 ml/g, preferably at least 0.20 ml/g, preferably between 0.25 ml/g and 0.80 ml/g, more preferably between 0.30 and 0.65 ml/g.

The median mesopore diameter is advantageously between 3 nm and 25 nm, preferably between 6 and 20 nm and particularly preferably between 8 and 18 nm.

The catalyst advantageously exhibits a median macropore diameter of between 50 and 1500 nm, preferably between 80 and 1000 nm and more preferably still of between 250 and 800 nm.

Preferably, the catalyst exhibits a low microporosity; very preferably, it does not exhibit any microporosity.

Aromatics Hydrogenation Process

Another subject of the present invention is a process for the hydrogenation of at least one aromatic or polyaromatic compound present in a hydrocarbon feedstock having a final boiling point of less than or equal to 650° C., generally between 20 and 650° C., and preferably between 20 and 450° C. Said hydrocarbon feedstock containing at least one aromatic or polyaromatic compound may be chosen from the following petroleum or petrochemical fractions: the reformate from catalytic reforming, kerosene, light gas oil, heavy gas oil, cracking distillates, such as FCC recycle oil, coking unit gas oil or hydrocracking distillates.

The content of aromatic or polyaromatic compounds present in the hydrocarbon feedstock treated in the hydrogenation process according to the invention is generally between 0.1% and 80% by weight, preferably between 1% and 50% by weight, and particularly preferably between 2% and 35% by weight, the percentage being based on the total weight of the hydrocarbon feedstock. The aromatic compounds present in said hydrocarbon feedstock are for example benzene or alkylaromatics, such as toluene, ethylbenzene, o-xylene, m-xylene or p-xylene, or also aromatics having several aromatic nuclei (polyaromatics), such as naphthalene.

The sulfur or chlorine content of the feedstock is generally less than 5000 ppm by weight of sulfur or chlorine, preferably less than 100 ppm by weight and particularly preferably less than 10 ppm by weight.

The technological implementation of the process for the hydrogenation of the aromatic or polyaromatic compounds is, for example, carried out by injection, as ascending or descending stream, of the hydrocarbon feedstock and of the hydrogen into at least one fixed bed reactor. Said reactor may be of isothermal type or of adiabatic type. An adiabatic reactor is preferred. The hydrocarbon feedstock can advantageously be diluted by one or more reinjection(s) of the effluent, resulting from said reactor where the aromatics hydrogenation reaction takes place, at various points of the reactor, located between the inlet and the outlet of the reactor, in order to limit the temperature gradient in the reactor. The technological implementation of the aromatics hydrogenation process according to the invention can also advantageously be carried out by the implantation of at least said supported catalyst in a reactive distillation column or in reactors-exchangers or in a slurry-type reactor. The stream of hydrogen may be introduced at the same time as the feedstock to be hydrogenated and/or at one or more different points of the reactor.

The hydrogenation of the aromatic or polyaromatic compounds can be carried out in the gas phase or in the liquid phase, preferably in the liquid phase. Generally, the hydrogenation of the aromatic or polyaromatic compounds is carried out at a temperature of between 30 and 350° C., preferably between 50 and 325° C., at a pressure of between 0.1 and 20 MPa, preferably between 0.5 and 10 MPa, at a hydrogen/(aromatic compounds to be hydrogenated) mole ratio between 0.1 and 10 and at an hourly space velocity HSV of between 0.05 and 500 $h^{-1}$, preferably between 0.1 and 10 $h^{-1}$, of a hydrocarbon feedstock containing aromatic or polyaromatic compounds and having a final boiling point of less than or equal to 650° C., generally between 20 and 650° C., and preferably between 20 and 450° C.

The hydrogen flow rate is adjusted in order to have available a sufficient amount thereof to theoretically hydrogenate all of the aromatic compounds and to maintain an excess of hydrogen at the reactor outlet.

The conversion of the aromatic or polyaromatic compounds is generally greater than 20 mol %, preferably greater than 40 mol %, more preferably greater than 80 mol % and particularly preferably greater than 90 mol % of the aromatic or polyaromatic compounds present in the hydrocarbon-based feedstock. The conversion is calculated by dividing the difference between the total moles of the aromatic or polyaromatic compounds in the hydrocarbon feedstock and in the product by the total moles of the aromatic or polyaromatic compounds in the hydrocarbon feedstock.

According to a specific alternative form of the process according to the invention, a process for the hydrogenation of the benzene of a hydrocarbon feedstock, such as the reformate resulting from a catalytic reforming unit, is carried out. The benzene content in said hydrocarbon feedstock is generally between 0.1 and 40% by weight, preferably between 0.5 and 35% by weight and particularly preferably between 2 and 30% by weight, the percentage by weight being based on the total weight of the hydrocarbon feedstock.

The sulfur or chlorine content of the feedstock is generally less than 10 ppm by weight of sulfur or chlorine respectively and preferably less than 2 ppm by weight.

The hydrogenation of the benzene contained in the hydrocarbon feedstock may be carried out in the gas phase or in the liquid phase, preferably in the liquid phase. When it is carried out in the liquid phase, a solvent may be present, such as cyclohexane, heptane or octane. Generally, the hydrogenation of the benzene is carried out at a temperature of between 30 and 250° C., preferably between 50 and 200° C. and more preferably between 80 and 180° C., at a pressure of between 0.1 and 10 MPa, preferably between 0.5 and 4 MPa, at a hydrogen/(benzene) mole ratio between 0.1 and 10 and at an hourly space velocity HSV of between 0.05 and 50 $h^{-1}$, preferably between 0.5 and 10 $h^{-1}$.

The conversion of the benzene is generally greater than 50 mol %, preferably greater than 80 mol %, more preferably greater than 90 mol % and particularly preferably greater than 98 mol %.

The invention will now be illustrated by the following examples which are in no way limiting.

EXAMPLES

For all the catalysts mentioned in the examples mentioned below, the support is an alumina A having a specific surface area of 80 $m^2/g$, a pore volume of 0.7 ml/g ($cm^3/g$) and a median mesopore diameter of 12 nm.

Example 1: Preparation of an Aqueous Solution of Ni Precursors

The aqueous solution of Ni precursors (solution S) used for the preparation of the catalysts A to E is prepared by dissolving 43.5 g of nickel nitrate ($NiNO_3$ (supplier Strem Chemicals®) in a volume of 13 ml of distilled water. The solution S, the Ni concentration of which is 350 g of Ni per liter of solution, is obtained.

Example 2: Catalyst A—20% by Weight of Ni (Comparative)

The solution S prepared in example 1 is impregnated under dry conditions on 10 g of alumina A. The solid thus obtained is subsequently dried in an oven overnight at 120° C. and then calcined under a stream of air of 1 l/h/g of catalyst at 450° C. for 2 hours. The calcined catalyst thus prepared contains 20% by weight of the nickel element relative to the total weight of the alumina-supported catalyst.

The catalyst precursor is then reduced under the conditions as described in example 8 below.

Example 3: Catalyst B—20% by Weight of Ni+ of Cu in Co-Impregnation with a Ni/Cu Ratio=3 (Comparative)

A copper nitrate solution is prepared so as to finally obtain a Ni/Cu ratio=3 on the final catalyst is dry-co-impregnated, with the solution S prepared in example 1, on 10 g of alumina A. The solid thus obtained is then dried in an oven overnight at 120° C. The solid thus obtained is then dried in an oven overnight at 120° C., then calcined under a stream of air of 1 l/h/g of catalyst at 450° C. for 2 hours.

The catalyst precursor is then reduced under the conditions as described in example 8 below.

Example 4: Catalyst C—Impregnation of Ni+Cu (5% by Weight Ni and Ni/Cu Mole Ratio=3) Followed by Impregnation of 20% by Weight of Ni (According to the Invention)

A copper nitrate solution is prepared so as to finally obtain a Ni/Cu ratio=3 on the intermediate catalyst and dry-co-impregnated with the solution S prepared in example 1, on 10 g of alumina A. The Ni content is 5% by weight relative to the weight of the final catalyst. The solid thus obtained is subsequently dried in an oven overnight at 120° C., and then calcined under a stream of air of 1 l/h/g of catalyst at 450° C. for 2 hours. This is then reduced under a hydrogen stream at 190° C. for 4 h then returned to air. The catalyst precursor C1 is obtained.

The solution S is then dry-impregnated on the catalyst precursor C1 so as to obtain 20% by weight of Ni alone, relative to the total weight of the final catalyst (which does not contribute to the alloy). The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 8 below.

Example 5: Catalyst D—Ni+Cu Impregnation (2% by Weight of Ni and Ni/Cu Mole Ratio=3) Followed by Impregnation of 20% by Weight of Ni (According to the Invention)

A copper nitrate solution is prepared so as to finally obtain a Ni/Cu ratio=3 on the intermediate catalyst and dry-co-impregnated with the solution S prepared in example 1, on 10 g of alumina A. The Ni content is 2% by weight relative to the weight of the final catalyst. The solid thus obtained is subsequently dried in an oven overnight at 120° C., and then calcined under a stream of air of 1 l/h/g of catalyst at 450° C. for 2 hours. This is then reduced under a hydrogen stream at 190° C. for 4 h. The catalyst precursor D1 is obtained.

The solution S is then dry-impregnated on the catalyst precursor D1 so as to obtain 20% by weight of Ni alone, relative to the total weight of the final catalyst (which does not contribute to the alloy). The solid thus obtained is subsequently dried in an oven overnight at 120° C., and then calcined under a stream of air of 1 l/h/g of catalyst at 450° C. for 2 hours. The catalyst precursor is then reduced under the conditions as described in example 8 below.

Example 6: Catalyst E—Ni+Cu Impregnation (5% by Weight of Ni and Ni/Cu Mole Ratio=2) Followed by Impregnation of 20% by Weight of Ni (According to the Invention)

A copper nitrate solution is prepared so as to finally obtain a Ni/Cu ratio=2 on the intermediate catalyst and dry-co-impregnated with the solution S prepared in example 1, on 10 g of alumina A. The Ni content is 5% by weight relative to the weight of the final catalyst. The solid thus obtained is subsequently dried in an oven overnight at 120° C., and then calcined under a stream of air of 1 l/h/g of catalyst at 450° C. for 2 hours. This is then reduced under a hydrogen stream at 190° C. for 4 h. The catalyst precursor E1 is obtained.

The solution S is then dry-impregnated on the catalyst precursor E1 so as to obtain 20% by weight of Ni alone, relative to the total weight of the final catalyst (which does not contribute to the alloy). The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 8 below.

Example 7: Characterization

All the catalysts contain the contents targeted during impregnation, that is to say 20% of nickel element (characterized by X-ray Fluorescence) relative to the total weight of the catalyst, and the % of copper added (characterized by X-ray Fluorescence).

The amount of alloy obtained after the calcination then reduction step was determined by X-ray diffraction (XRD) analysis on samples of the catalyst in powder form.

The amount of nickel in metallic form obtained after the reduction step was determined by X-ray diffraction (XRD) analysis on samples of catalyst in powder form. Between the reduction step and throughout the duration of the characterization by XRD, the catalysts are never returned to the open air. The diffraction patterns are obtained by radiocrystallographic analysis by means of a diffractometer using the conventional powder method with $K\alpha 1$ radiation of copper ($\lambda$=1.5406 Å).

The degree of reduction was calculated by calculating the area of the line of $Ni^0$ located around 52° 2θ, on all of the diffractograms of each sample of catalyst analyzed, then by subtracting the signal present as soon as ambient temperature is reached under the line at 52°, which is due to alumina.

Table 1 below collates the degrees of reduction or else the content of nickel metal $Ni^0$ (expressed as % by weight relative to the total weight of Ni) for all the catalysts A to E characterized by XRD after a reduction step at 190° C. for 90 minutes under a hydrogen stream. These values were also compared with the degree of reduction obtained for catalyst A (Ni alone) after a conventional reduction step (that is to say at a temperature of 400° C. for 15 hours under a hydrogen stream).

Alumina in delta and theta form and large CuO and NiO lines are detected at ambient temperature on all the copper- and nickel-containing catalysts, after calcination.

A line corresponding to the alloy in $Ni_{0.76}Cu_{0.24}$ form is moreover detected after reduction.

In order to evaluate the degree of reducibility and therefore the formation of $Ni^0$, the area of the line of $Ni^0$ located around 52° 2θ is measured, on all the diffractograms, by subtracting the signal present from ambient temperature under the line at 52° and which is due to the alumina. It is thus possible to determine the relative percentage of $Ni^0$ crystallized after reduction.

Table 1 below summarizes the degrees of reducibility or the $Ni^0$ content for all the catalysts characterized by XRD after reduction at 190° C. for 90 minutes under a hydrogen stream. These values were also compared with the degree of reduction obtained for catalyst A (Ni alone) after a conventional reduction step (that is to say at a temperature of 400° C. for 15 hours under a hydrogen stream).

TABLE 1

| Catalyst | Final reduction | Ni content for the 1st imp. (wt %) | Ni content for the 2nd imp. (wt %) | Ni/Cu alone mole ratio | Percentage of $Ni^0$ (XRD) after reduction (%) |
|---|---|---|---|---|---|
| A (comparative) | 400° C., 15 h | — | 20 | — | 80 |
| A (comparative) | 190° C., 90 min | — | 20 | — | 0* |
| B (comparative) | 190° C., 90 min | 20 | — | 3 | 0** |
| C (invention) | 190° C., 90 min | 5 | 20 | 3 | 100 |
| D (invention) | 190° C., 90 min | 2 | 20 | 3 | 90 |
| E (invention) | 190° C., 90 min | 5 | 20 | 2 | 80 |

*Nickel in NiO form
**Nickel in alloy form only

For catalyst A (20% Ni alone/alumina), the degree of nickel reducibility is 0% after exactly the same reduction treatment under hydrogen as for the catalysts B to E.

The pre-impregnation of nickel (5% by weight of Ni) and of copper with a Ni/Cu ratio of 2 makes it possible to obtain reduced $Ni^0$ of the order of 80% in the end on the catalyst. The pre-impregnation of less NiCu alloy with a content of nickel making up the alloy of 2% by weight and of copper with a Ni/Cu ratio of 3 makes it possible to obtain reduced $Ni^0$ of the order of 90% in the end on the catalyst. The pre-impregnation of nickel (5% by weight of Ni) and of copper with a Ni/Cu ratio of 3 makes it possible to obtain 100% of reduced $Ni^0$ from 190° C. in the end on the catalyst.

Example 8: Catalytic Tests: Performance Levels in Hydrogenation of Toluene

Catalysts A to E described in the examples above are also tested with regard to the reaction for the hydrogenation of toluene.

The hydrogenation reaction is carried out in a 500 ml stainless steel autoclave which is provided with a magnetically-driven mechanical stirrer and which is able to operate under a maximum pressure of 100 bar (10 MPa) and temperatures of between 5° C. and 200° C.

216 ml of n-heptane (supplied by VWR®, purity >99% Chromanorm HPLC) and 2 ml of catalyst (for catalysts from A to E) are added to an autoclave. The autoclave is then pressurized under 35 bar (3.5 MPa) of hydrogen. The catalyst is first reduced in situ, at 190° C. under a hydrogen pressure for 90 minutes (temperature rise gradient of 1° C./min) for catalysts A to E (which corresponds to step h) of the process for preparation of the catalyst according to the invention according to one embodiment).

The autoclave is then brought to the test temperature equal to 80° C. At time t=0, approximately 26 g of toluene (supplied by SDS®, purity >99.8%) are introduced into the autoclave (the initial composition of the reaction mixture is then toluene 6 wt %/n-heptane 94 wt %) and stirring is started at 1600 rev/min. The pressure is kept constant at 35 bar (3.5 MPa) in the autoclave using a storage cylinder located upstream of the reactor.

Another test was carried out for catalyst A, but with a catalyst reduction temperature of 400° C. for 15 hours.

The progress of the reaction is monitored by taking samples from the reaction medium at regular time intervals: the toluene is completely hydrogenated to give methylcyclohexane. The hydrogen consumption is also monitored over time by the decrease in pressure in a storage cylinder located upstream of the reactor.

The catalytic activities measured for catalysts A to E are reported in table 2 below. They are related to the catalytic activity ($A_{HARO}$) measured for catalyst A prepared under conventional reduction conditions (at a temperature of 400° C. for 15 hours under a hydrogen stream).

TABLE 2

| Catalyst | Final reduction | Ni content for the 1st imp. (wt %) | Ni content for 2nd imp. (%) | Ni/Cu ratio | Percentage of Ni° (XRD) after reduction (%) | $A_{HARO}$ (%) |
|---|---|---|---|---|---|---|
| A (comparative) | 400° C., 15 h | — | 20 | — | 80 | 100 |
| A (comparative) | 190° C., 90 min | — | 20 | — | 0 | 0 |
| B (comparative) | 190° C., 90 min | 20 | — | 3 | 0 | 10 |
| C (invention) | 190° C., 90 min | 5 | 20 | 3 | 100 | 210 |
| D (invention) | 190° C., 90 min | 2 | 20 | 3 | 90 | 150 |
| E (invention) | 190° C., 90 min | 5 | 20 | 2 | 80 | 100 |

This clearly shows the improved performance of catalysts C, D and E according to the invention, compared with the catalyst Ni alone on alumina reduced at 190° C. for 90 min, which is completely inactive. Moreover, it should be noted that the NiCu alloy alone (catalyst B) has an activity which is very much behind the reference (of the order of 10%).

The invention claimed is:

1. A process for preparing a catalyst for the hydrogenation of aromatic or polyaromatic compounds comprising nickel, in a proportion of 20% to 45% by weight of nickel element relative to the total weight of the catalyst, and copper, in a proportion of 0.5% to 15% by weight of copper element relative to the total weight of the catalyst, and a support comprising at least one refractory oxide chosen from silica, alumina and silica-alumina, said process consisting of the following steps:
   a) a step of bringing the support into contact with at least one solution consisting of, as metal precursors in said solution, of at least one copper precursor and one nickel precursor at a desired nickel concentration in order to obtain, on the final catalyst, a content of between 0.5% and 15% by weight of nickel element relative to the total weight of the final catalyst;
   b) at least one step of drying the catalyst precursor resulting from step a) at a temperature of less than 250° C.;
   c) optionally, a heat treatment of the catalyst precursor obtained at the end of step b) at a temperature of between 250 and 1000° C., in the presence or absence of water;
   d) the catalyst precursor resulting from step b), or optionally step c), is reduced by bringing said catalyst precursor into contact with a reducing gas at a temperature of between 150 and 250° C.;
   e) a step of bringing the catalyst precursor obtained at the end of step d) into contact with a solution consisting of, as a metal precursor in said solution, of at least one nickel precursor;
   f) at least one step of drying the catalyst precursor resulting from step e) at a temperature of less than 250° C.;
   g) optionally, a heat treatment of the catalyst precursor obtained at the end of step f) at a temperature of between 250 and 1000° C., in the presence or absence of water;
   h) the catalyst precursor resulting from step f), or optionally step g), is reduced by bringing said catalyst precursor into contact with a reducing gas at a temperature of between 150 and 250° C.

2. The process as claimed in claim 1, wherein, in step a), the mole ratio between nickel and copper is between 0.5 and 5.

3. The process as claimed in claim 1, wherein step d) and/or h) is (are) carried out at a temperature of between 160 and 230° C.

4. The process as claimed in claim 1, wherein step d) and/or h) is (are) carried out at a temperature of between 170 and 220° C.

5. The process as claimed in claim 1, wherein steps d) and/or h) is (are) carried out for between 10 minutes and 110 minutes.

6. The process as claimed in claim 1, also comprising a step of passivation of the catalyst precursor with a sulfur-containing compound after the reduction step d) but before step e), and/or after the reduction step h).

7. The process as claimed in claim 6, wherein the passivation step(s) is (are) carried out at a temperature of between 20 and 350° C. for 10 to 240 minutes.

8. The process as claimed in claim 6, wherein said sulfur-containing compound is chosen from thiophene, thiophane, dimethyl sulfide, diethyl sulfide, dipropyl sulfide, propylmethyl sulfide and dithiodiethanol.

9. The process as claimed in claim 1, wherein the copper precursor is chosen from copper acetate, copper acetylacetonate, copper nitrate, copper sulfate, copper chloride, copper bromide, copper iodide and copper fluoride.

10. The process as claimed in claim 9, wherein the copper precursor is copper nitrate.

11. The process as claimed in claim 1, wherein the reducing gas of step d) and/or h) is dihydrogen.

12. The process as claimed in claim 11, wherein the dihydrogen flow rate, expressed in l/hour/gram of catalyst precursor, is between 0.01 and 100 l/hour/gram of catalyst precursor.

13. The process as claimed in claim 1, wherein the nickel precursor supplied during step a) and/or e) is chosen from nickel nitrate, nickel carbonate and nickel hydroxide.

14. The process as claimed in claim 1, wherein the solution in step a) and/or e) are independently aqueous or organic solutions, or a mixture of water and at least one organic solvent.

15. The process as claimed in claim 1, wherein the solution in step a) and/or e) are independently aqueous or organic solutions, or a mixture of water and at least one organic solvent, wherein the organic solution contains methanol, ethanol, phenol, acetone, toluene or dimethyl sulfoxide.

16. The process as claimed in claim 1, wherein the solution in step a) and/or e) are aqueous solutions.

17. A process for the hydrogenation of at least one aromatic or polyaromatic compound present in a hydrocarbon feedstock having a final boiling point of less than or equal to 650° C., said process being carried out in the gas phase or in the liquid phase, at a temperature of between 30 and 350° C., at a pressure of between 0.1 and 20 MPa, at a hydrogen/(aromatic compounds to be hydrogenated) mole ratio between 0.1 and 10 and at an hourly space velocity HSV of between 0.05 and 50 $h^{-1}$, in the presence of a catalyst obtained as claimed in claim 1.

* * * * *